United States Patent [19]
Hoffmann

[11] Patent Number: 5,777,122
[45] Date of Patent: Jul. 7, 1998

[54] ENANTIOMERICALLY PURE QUINUCLIDINE DERIVATIVES AND METHODS FOR THEIR PRODUCTION AND USE

[75] Inventor: H. Martin R. Hoffmann, Hanover, Germany

[73] Assignee: Buchler GmbH, Brunswick, Germany

[21] Appl. No.: 795,199

[22] Filed: Feb. 5, 1997

[30] Foreign Application Priority Data

Feb. 7, 1996 [DE] Germany .................. 196 04 395.6

[51] Int. Cl.[6] ............ C07D 453/02; C07D 453/04; C07F 7/08
[52] U.S. Cl. ............ 546/133; 546/14; 546/136
[58] Field of Search .................... 546/133, 136, 546/14

[56] References Cited

U.S. PATENT DOCUMENTS 4,093,619  6/1978  Jarreau et al. .................. 260/284

FOREIGN PATENT DOCUMENTS 1 472 016  1/1967  France .................. 546/132
2 332 278  7/1977  France .
2 332 279  7/1977  France .

OTHER PUBLICATIONS

Hoffmann et al.,Chemical Abstracts,vol. 125(15)abst.No. 196,082v,Oct. 7, 1996.
Hoffmann et al.,Chemical Abstracts,vol. 125(5),abst.No. 50,212,Jul. 29, 1996.
Tetrahedron Letters No. 29, Oxford GB, pp. 2471–2474. G.A. Epling et al. (1977).
Chemical Abstracts, vol. 118, No. 19, May 10, 1993 pp. 923–927, A.M. Gazaliev et al.
Chemical Abstracts, vol. 108, No. 19, May 9, 1988 pp. 911–922, Y. Yanuka et al.
R.O. Hutchins, K. Learn, F. El–Telbany, Y.P. Stercho, J. Org. Chem. 1984, 49, 2438.
S. Kim, H.J. Kang, S. Yang, Tetrahedron Lett. 1984, 25, 2985.
Organic Chemistry, Third Edition, International Student Edition, 1970, pp. 425, 458 and 459.
J. Málek, M. Černý, Syntheses 1972, 218.
H. Haubenstock, J. Org. Chem. 1973, 38, 1765.
H.C. Brown, S. Krishnamurthy, Tetrahedron 1979, 35, 567.
M. Muraki, T. Mukaiyama, Chemistry Lett. 1974, 1447.
M. Muraki, T. Mukaiyama, Chemistry Lett. 1975, 875.
R. Kanzawa, T. Tokoroyama, Syntheses 1976, 526.
J.S. Cha, J.C. Lee, H.S. Lee, S.E. Lee, J.M. Kim. O.O. Kwon, S.J. Min, Tetrahedron Lett. 1991, 32, 6903.
J.K. Ruff, M.F. Hawthorne, J. Am. Chem. Soc. 1959, 2141.
H.C. Brown and C. J. Shoaf, J. Am. Chem. Soc. 1964, 1079.
J. Koenig et al., "Nouvelle Modification de la Methode D'Oxydation Selon Oppenauer: Application a la Quinine", Tetrahedron Let., No. 31, (1978), pp. 2779–2782.
G. A. Epling et al., "Photolysis of Cinchona Alkaloids. Photochemical Degradation to 5–Vinyl–quinuclidine–2–Carboxaldehyde, A Precursor to Synthetic Antimalarials", Tetrahedron Let. No. 29, (1979), pp. 2471–2474.
K. Koch et al., "Hydroxy–Directed Hydroaluminations: A Stereoselective Approach to Cycloalkanols from β–Aryl Enones", Tetrahedron Let., vol. 35, No. 8, (1994), pp. 1137–1140.
M. S. Ashwood et al., "Synthesis of the Selective Muscarinic Agonist (3R)–3–(6–chloropyrazin–2–yl)–1–azabicyclo [2.2.2]octane", J. Chem. Soc. Perkin Trans., (1985), pp. 641–644.
J. Boivin et al., "GIF Oxidation of some Alicyclic Amines", Tetrahedron Let., vol. 31, No. 16, (1990), pp. 2281–2282.

*Primary Examiner*—Alan L. Rotman
*Attorney, Agent, or Firm*—Foley & Lardner

[57] ABSTRACT

A process for cleaving cinchona alkaloids to a quinoline derivative and an enantiomerically pure, functionalized 1-azabicyclo(2.2.2)octane, includes treating a cinchona alkaloid with a complex metal hydride while simultaneously oxidizing by exposure to air in an ether or tetrahydrofuran. Enantiomerically pure 1-azabicyclo(2.2.2)octanes of the formula

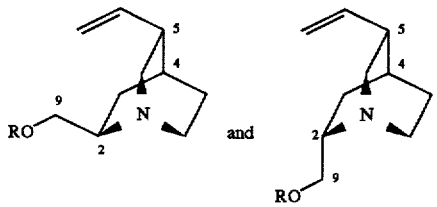

in which R is hydrogen, a straight-chain or branched alkoxycarbonyl group with 1 to 12 carbon atoms, a straight-chain or branched alkyl group with 1 to 12 carbon atoms, alkylated silyl groups, or a substituted phenyl or benzyl substituent, are also provided.

10 Claims, No Drawings

1

ENANTIOMERICALLY PURE QUINUCLIDINE DERIVATIVES AND METHODS FOR THEIR PRODUCTION AND USE

BACKGROUND OF THE INVENTION

1. Field of the Invention

The invention relates to novel enantiomerically pure quinuclidine derivatives, to processes for their preparation, and to methods for their use, for example, as intermediates in drug synthesis, and as a ligand as well as catalyst in asymmetric syntheses.

2. Description of Related Art

Muscarine stimulates postganglionic parasympathetic receptors and therefore has great importance for experimental pharmacology. However, it is not used therapeutically. Quinuclidine derivatives are muscarine agonists which, it is assumed, may be effective for the treatment of Alzheimer's disease.

Tetrahedron Let. No. 31 (1978), pages 2779–2782 describes the conversion of quinine into quinidine by oxidation. FR 1 472 016 relates to a process for preparing compounds by substitution on the quinuclidine nucleus. Quinuclidine as such is obtained in this case, no elimination of the quinoline portion taking place. Tetrahedron Let. 31, No. 16 (1990), pages 2281–2282 describes simultaneous reaction of quinine with a reducing agent (zinc dust) and an oxidizing agent (air), and once again there is no elimination of quinoline. Tetrahedron Let. 35, No. 8 (1994), pages 1137–1140 proposes the conversion of a quinuclidine derivative in enone form into the corresponding alkanol by reduction with LiAlH$_4$ in THF in order to carry out a stereoselective reduction. Tetrahedron Let. No. 29 (1977), pages 2471–2474 describes the photolysis of cinchona alkaloids, resulting in mixtures of epimeric aldehydes, which are not separable and undergo spontaneous interconversion. Furthermore, the reduction of these aldehydes by sodium borohydride is described, resulting in a 1-azabicyclo (2.2.2)octane as a mixture of pseudoenantiomers.

J. Chem. Soc. Perkin Trans. I 1995, 641–644 proposes the preparation of 3-substituted quinuclidines by intramolecular N-alkylation of suitable piperidine derivatives. To obtain enantiomerically pure 1-azabicyclo(2.2.2)octanes hitherto, appropriate chiral piperidines have been prepared as precursors and then cyclized, for example in accordance with the following equation.

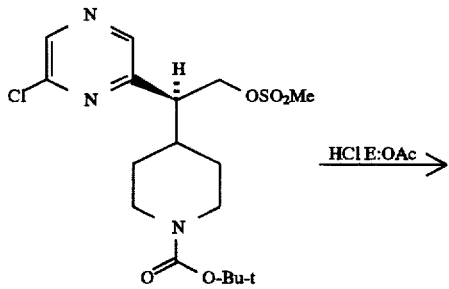

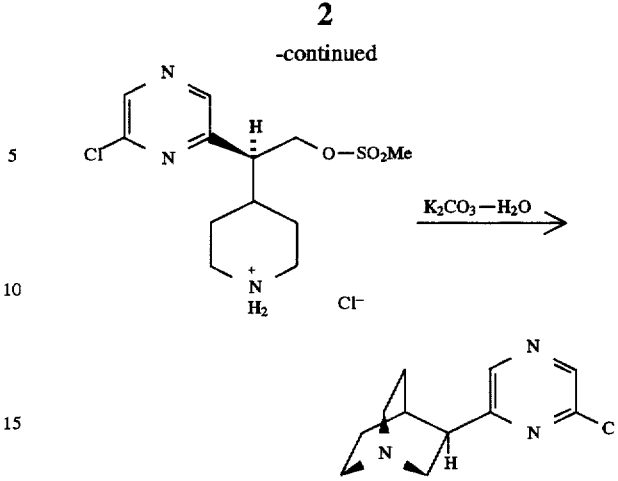

However, this process is disadvantageous because of the need first to prepare chiral precursor compounds.

SUMMARY OF THE INVENTION

One object of the present invention is to prepare substituted quinuclidine derivatives in enantiomerically pure form while avoiding the preparation of chiral precursor compounds.

It is also an object of the invention to provide enantiomerically pure quinuclidine derivatives and methods for their use.

These objects are achieved by providing in accordance with the present invention a process for cleaving cinchona alkaloids to a quinoline derivative and an enantiomerically pure 1-azabicyclo(2.2.2)octane, which includes treating a cinchona alkaloid with a complex metal hydride while simultaneously oxidizing by exposure to air in an ether, such as tetrahydrofuran.

These objects are also achieved by providing in accordance with the present invention enantiomerically pure 1-azabicyclo(2.2.2)octanes of the formula

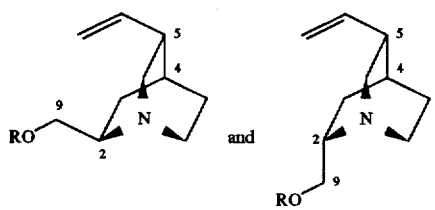

in which R is hydrogen, a straight-chain or branched alkoxycarbonyl group with 1 to 12 carbon atoms, a straight-chain or branched alkyl group with 1 to 12 carbon atoms, alkylated silyl, or a substituted phenyl or benzyl substituent.

Further objects, features and advantages of the invention will become apparent from the detailed description that follows.

DETAILED DESCRIPTION OF THE PREFERRED EMBODIMENTS

The process according to the invention permits direct access to 4 of the 5 chiral centers in the natural substance, i.e., the configuration of the bridged atoms N(1) and C(4) and of the branch points at C(3) and C(8) of the natural substance (traditional numbering of the atoms by Rabe) is retained in the eliminated 1-azabicyclo(2.2.2)octane (N(1), C(4), C(5) and C(2)) and is defined. De novo synthesis of the 1-azabicyclo(2.2.2)octane framework from enantiomerically pure precursors is unnecessary.

In the process according to the invention, the cinchona alkaloids, e.g. quinine, quinidine, cinchonine and cinchonidine are reduced by complex metal hydrides. Any such hydrides or mixtures thereof can be used. For example, LiAlH$_4$ and its alkoxy derivatives LiAlH$_2$(OR)$_2$ with R=C$_1$ to C$_6$ can be employed. The simultaneous oxidation is brought about by exposing the reaction mixture to air. The reaction takes place in anhydrous organic solvents in which reductions with complex metal hydrides are normally carried out. Preferably employed are anhydrous ethers, especially tetrahydrofuran. Addition of TMEDA is optional.

Enantiomerically pure 1-azabicyclo(2.2.2)octanes according to the invention have the general formulae

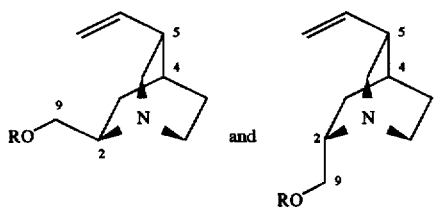

in which R is hydrogen, a straight-chain or branched alkoxycarbonyl group with 1 to 12 carbon atoms, a straight-chain or branched alkyl group with 1 to 12 carbon atoms, alkylated silyl groups such as tert-butyldimethylsilyl or a substituted phenyl or benzyl substituent.

Examples of compounds obtained according to the invention include (2R,5R)-2-(t-butoxycarbonyloxymethyl)-5-ethenyl-1-azabicyclo(2.2.2)octane (2b), (2R,5R,9R/S)-2-(t-butoxycarbonyloxymethyl)-9-deuterio-5-ethenyl-1-azabicyclo(2.2.2)octane (4a, 4b), (2S,5R)-2-(t-butoxycarbonyloxymethyl)-5-ethenyl-1-azabicyclo(2.2.2)octane (6b), (2S,5R,9R/S)-2-(t-butoxycarbonyloxymethyl)-9-deuterio-5-ethenyl-1-azabicyclo(2.2.2)octane (7a, 7b).

These compounds are valuable intermediates for preparing medicinal substances such as muscarine agonists.

A preferred synthetic route for the process according to the invention is depicted below.

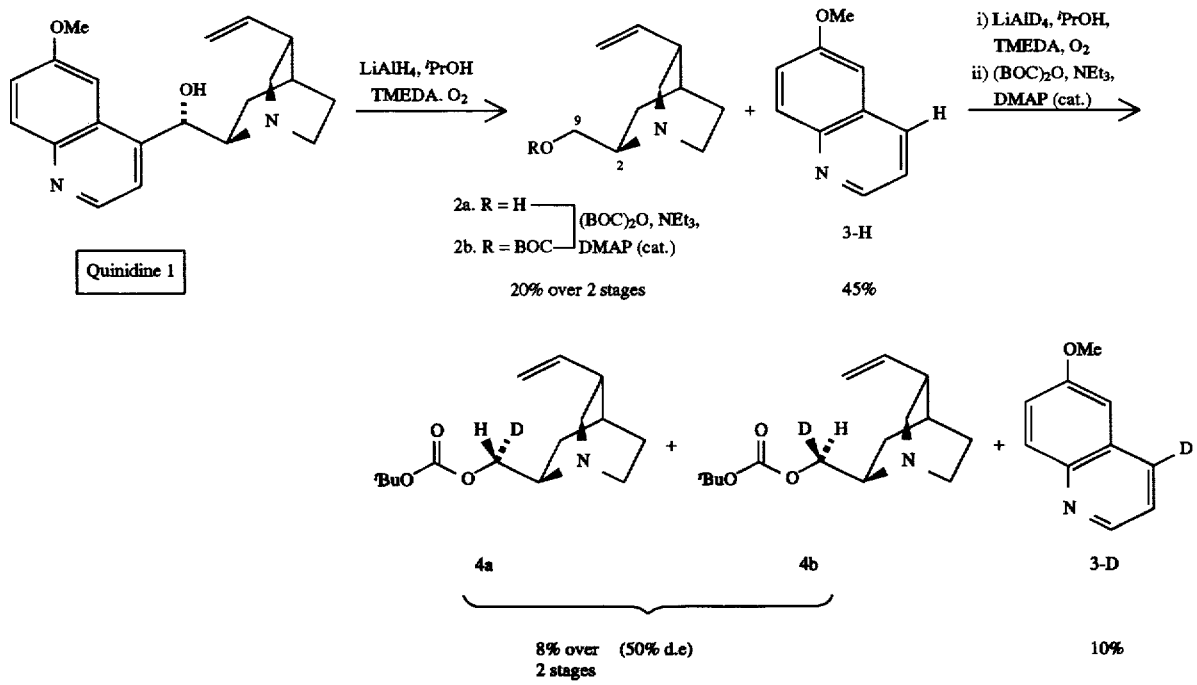

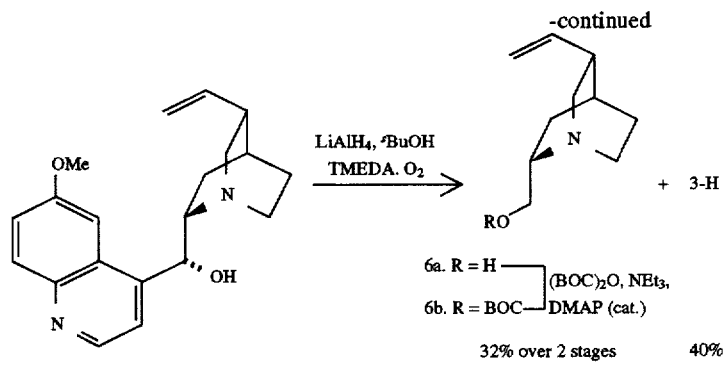

32% over 2 stages          40%

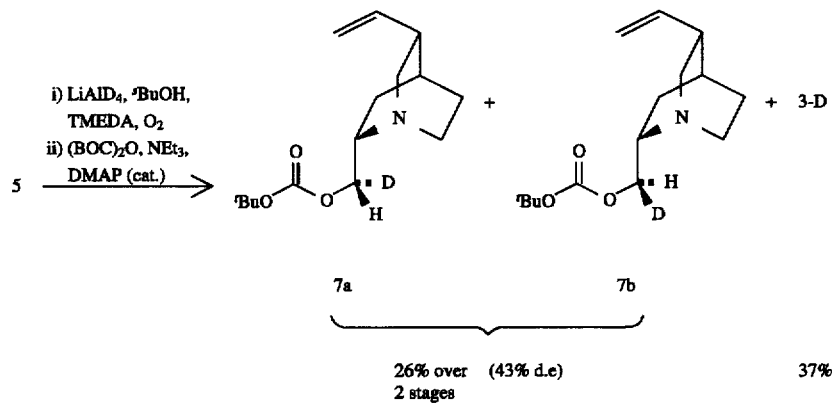

26% over     (43% d.e)          37%
2 stages

The invention is illustrated by the following non-limiting examples.

EXAMPLES

A 50 ml round-bottom flask is charged with dry THF (14 ml) and LiAlH$_4$ (304 mg, 8 mmol) or LiAlD$_4$ (336 mg, 8 mmol). A secondary alcohol, sec-butanol, and tetramethylethylenediamine (TMEDA) (0.60 ml, 4 mmol) are added at 0° C. A cinchona alkaloid (649 mg, 2 mmol) is added in several portions at 0° C. The mixture is stirred at room temperature while exposing to air (drying tube) for 4 days and worked up by successive addition of ethyl acetate (0.29 ml), water (0.3 ml) and 2N NaOH (0.3 ml). The resulting precipitate is filtered off and thoroughly washed with CH$_2$Cl$_2$. After removal of the solvent, the residue is taken up in CH$_2$Cl$_2$ and dried (for example over sodium sulfate).

CH$_2$Cl$_2$ is removed and the resulting viscous yellow oil is dried in vacuo and taken up in dry CH$_2$Cl$_2$ (4 ml). The solution is treated with triethylamine (0.84 ml, 6 mmol), bis-tert-butyl dicarbonate (1.38 ml, 6 mmol) and dimethylaminopyridine in catalytic amounts and stirred at room temperature overnight. The crude mixture of products is adsorbed onto silica gel and chromatographed with a diethyl ether/petroleum ether (1:2) mixture as eluent. The isolated products are obtained as pale yellow oils.

Experimental Data (2R,5R)-2-(t-Butoxycarbonyloxymethyl)-5-ethenyl-1-azabicyclo(2.2.2)octane (2b) and 6-methoxyquinoline (3-H).

Reducing agent: LiAlH$_4$, secondary alcohol: i-PrOH (1.07 ml, 14 mmol), cinchona alkaloid: quinidine, yield: 107 mg (20%) of 2b and 143 mg (45%) of 3-H.

Data for 2b: $[\alpha]_D^{20}$=+91.4° (c=1.25, CHCl$_3$). IR (cap. film): ν=793, 864, 913, 1097, 1164, 1256, 1278, 1370, 1456, 1741, 2873, 2938, 2978, 3077 cm$^{-1}$, $^1$H NMR (200 MHz, CDCl$_3$): δ=1.20–1.36 (m, 1H-3), 1.40–1.68 (m, 3H-8,8,3), 1.47 (s, 9H-t-BuO), 1.71–1.80 (m, 1H-4), 2.17–2.34 (m, 1H-5), 2.71 (ddd, $^2$J=14 Hz, $^3$J=7 Hz, $^4$J=2 Hz, 1H-6), 2.78–3.15 (m, 4H-7,7,6,2), 3.94 (dd, $^2$J=11 Hz, $^3$J=5 Hz, 1H-9), 4.08 (dd, $^2$J=11 Hz, $^3$J=9 Hz, 1H-9), 5.02 (ddd, $^2$J=1 Hz, $^3$J$_{trans}$=17 Hz, $^4$J=1 Hz, 1H-11), 5.04 (ddd, $^2$J=1 Hz, $^3$J$_{cis}$=11 Hz, $^4$J=1 Hz, 1H-11), 5.74–5.95 (m, 1H-10). $^{13}$C NMR (50 MHz, APT, CDCl$_3$): δ=24.06 (+, c-3), 26.72 (+, c-8), 27.47 (–, c-4), 27.75 (–, 3Me), 39.81 (–, C-5), 47.35 (+, C-7), 48.99 (+, C-6), 54.31 (–, C-2), 66.92 (+, C-9), 81.90 (+, 4° C.), 114.61 (+, C-11), 140.31 (–, C-10), 153.72 (+, C=O). MS-MAT (RT): m/z (%): 267 (33) [M$^+$], 211 (14), 194 (18), 170 (16), 159 (13), 150 (57), 136 (100), 116 (14), 102 (21). HRMS calculated for C$_{15}$H$_{25}$NO$_3$: 267.1834, found 267.1835.

Data for 3-H: IR (cap. film): ν=836, 848, 1027, 1038, 1128, 1163, 1231, 1270, 1500, 1597, 1624, 1698, 1741, 2934, 2975, 3377 cm$^{-1}$. $^1$H NMR (200 MHz, CDCl$_3$): δ=3.85 (s, 3H-MeO), 6.98 (d, $^4$J=3 Hz, 1H-5), 7.28 (dd, $^3$J=8.4 Hz, 1H-3), 7.34 (dd, $^3$J=9 Hz, $^4$J=3 Hz, 1H-7), 7.96 (dd, $^3$J=8 Hz, $^4$J=2 Hz, 1H-4), 8.00 (d, $^3$J=9 Hz, 1H-8), 8.74 (dd, $^3$J=4 Hz, $^4$J=2 Hz, 1H-2). $^{13}$C NMR (50 MHz, APT, CDCl$_3$): δ=55.41 (–, MeO), 105.05 (–, C-7), 121.30 (–, C-3), 122.23 (–, C-5), 129.25 (+, C-9), 130.76 (–, C-8), 134.71 (–, C-4), 144.36 (+, C-10), 147.85 (–, C-2), 157.64 (+, C-6). MS-MAT (RT): m/z (%): 159 (100) [M$^+$], 144 (7), 129 (13), 116 (52), 101 (3), 89 (16), 80 (3), 75 (4). HRMS calculated for C$_{10}$H$_9$NO: 159.0684, found 159.0683.

(2R,5R,9R/S)-2-(t-Butoxycarbonyloxymethyl)-9-deuterio-5-ethenyl-1-azabicyclo(2.2.2)octane (4a+4b) and 4-deuterio-6-methoxyquinoline (3-D). Reducing agent: LiAlD₄, secondary alcohol: i-PrOH (1.07 ml, 14 mmol), cinchona alkaloid: quinidine, yield: 43 mg (8%) of 4a+4b (50% d.e.) and 32 mg (10%) of 3-D.

Data for 4a+4b: IR (cap. film): v=793, 859, 913, 990, 1165, 1256, 1278, 1370, 1456, 1741, 2873, 2937, 2978, 3077 cm⁻¹. ¹H NMR (200 MHz, CDCl₃): δ=1.20–1.36 (m, 1H-3), 1.40–1.68 (m, 3H-8,8,3), 1.47 (s, 9H-t-BuO), 1.71–1.80 (m, 1H-4), 2.17–2.34 (m, 1H-5), 2.71 (ddd, ²J=14 Hz, ³J=7 Hz, ⁴J=2 Hz, 1H-6), 2.78–3.15 (m, 4H-7,7,6,2), 3.93 (bd, ³J=5 Hz, 1H-9), 4.06 (bd, ³J=9 Hz, 1H-9), 5.02 (ddd, ²J=1 Hz, ³J$_{trans}$=17 Hz, ⁴J=1 Hz, 1H-11), 5.04 (ddd, ²J=1 Hz, ³J$_{cis}$=11 Hz, ⁴J=1 Hz, 1H-11), 5.74–5.95 (m, 1H-10). ¹³C NMR (50 MHz, BB, CDCl₃): δ=24.16 (C-3), 26.81 (C-8), 27.59 (C-4), 27.82 (3Me), 39.87 (C-5), 47.54 (C-7), 49.09 (C-6), 54.37 (C-2) 66.34, 66.79, 67.24 (C-9), 81.93 (4° C.), 114.63 (C-11), 140.39 (C-10), 153.80 (C=O). MS-MAT (RT): m/z (%): 268 (27) [M⁺], 212 (17), 195 (17), 171 (16), 151 (57), 136 (100), 117 (11). HRMS calculated for C₁₅H₂₄DNO₃: 268.1896, found 268.1896.

Data for 3-D: IR (cap. film): v=710, 833, 875, 1029, 1121, 1152, 1230, 1262, 1300, 1373, 1430, 1468, 1500, 1584, 1620, 1747, 1936, 2938, 2960, 3392 cm⁻¹. ¹H NMR (200 MHz, CDCl₃): δ=3.89 (S, 3H-MeO), 7.03 (d, ⁴J=3 Hz, 1H-5), 7.32 (d, ³J=4 Hz, 1H-3), 7.36 (dd, ³J=9 Hz, ⁴J=3 Hz, 1H-7), 7.99 (d, ³J=9 Hz, 1H-8), 8.75 (d, ³J=4 Hz, 1H-2). ¹³C NMR (50 MHz, BB, CDCl₃): δ=54.46 (MeO), 104.13 (C-7), 120.18 (C-3), 121.20 (C-5), 128.23 (C-9), 129.82 (C-8), 132.89, 133.38, 133.87 (C-4), 143.45 (C-10), 146.88 (C-2), 156.75 (C-6). MS-MAT (RT): m/z (%): 160 (100) [M⁺], 145 (6), 130 (11), 117 (50), 103 (3), 90 (12), 80 (4), 76 (2). HRMS calculated for C₁₀H₈DNO: 160.0746, found 160.0745.

(2S,5R)-2-(t-Butoxycarbonyloxymethyl)-5-ethenyl-1-azabicyclo(2.2.2)octane (6b) and 6-methoxyquinoline (3-H). Reducing agent: LiAlH₄, secondary alcohol: s-BuOH (1.28 ml, 14 mmol), cinchona alkaloid: quinine, yield: 171 mg (32%) of 6b and 127 mg (40%) of 3-H.

Data for 6b: [α]$_D^{20}$=+29.4° (c=1.38, CHCl₃). IR (cap. film): v=794, 865, 912, 1097, 1165, 1256, 1278, 1370, 1396, 1455, 1475, 1741, 2865, 2937, 2978, 3077 cm⁻¹. ¹H NMR (200 MHz, CDCl₃): δ=0.85–1.02 (m, 1H-3), 1.41–1.61 (m, 2H-8), 1.47 (s, 9H-t-BuO), 1.70–1.80 (m, 1H-4), 1.80–1.97 (m, 1H-3), 2.21–2.39 (m, 1H-5), 2.60–2.80 (m, 2H-7,6) 2.90–3.16 (m, 2H-7,2), 3.19 (dd, ²J=13 Hz, ³J=10 Hz, 1H-6), 3.97 (dd, ²J=11 Hz, ³J=6 Hz, 1H-9), 4.08 (dd, ²J=11 Hz, ³J=9 Hz, 1H-9) 5.03 (ddd, ²J=1 Hz, ³J$_{cis}$=11 Hz, ⁴J=1 Hz, 1H-11), 5.04 (ddd, ²J=1 Hz, J$_{trans}$=17 Hz, ⁴J=1 Hz, 1H-11) 5.77–5.98 (m, 1H-10). ¹³C NMR (75 MHz, APT, CDCl₃): δ=24.91 (+, C-3), 27.35 (–, C-4), 27.72 (–, 3Me), 27.79 (+, C-8), 39.71 (–, C-5), 40.96 (+, C-7), 54.42 (–, C-2), 55.73 (+, C-6), 67.60 (+, C-9), 81.90 (+, 4° C.), 114.29 (+, C-11), 141.73 (–, C-10), 153.69 (+, C=O). MS-MAT (RT): m/z (%): 267 (37) [M⁺], 252 (17), 226 (3), 211 (28), 194 (34), 182 (7), 170 (32), 159 (48), 150 (51), 144 (28), 136 (100), 129 (30), 116 (46), 108 (29), 95 (30), 89 (30), 79 (35). HRMS calculated for C₁₅H₂₅NO₃: 267.1834, found 267.1834.
Data for 3-H: see above.

(2S,5R,9R/S)-2-(t-Butoxycarbonyloxymethyl)-9-deuterio-5-ethenyl-1-azabicyclo(2.2.2)octane (7a+7b) and 4-deuterio-6-methoxyquinoline (3-D). Reducing agent: LiAlD₄, secondary alcohol: s-BuOH (0.55 ml, 6 mmol), cinchona alkaloid: quinine, yield: 140 mg (26%) of 7a+7b (43% d.e.) and 119 mg (37%) of 3-D.

Data for 7a+7b: IR (cap. film): v=794, 857, 913, 1049, 1165, 1256, 1278, 1370, 1395, 1456, 1741, 2867, 2937, 2978, 3078 cm⁻¹. ¹H NMR (200 MHz, CDCl₃): δ=0.85–1.02 (m, 1H-3), 1.41–1.61 (m, 2H-8), 1.47 (s, 9H-t-BuO), 1.70–1.80 (m, 1H-4), 1.80–1.97 (m, 1H-3), 2.21–2.39 (m, 1H-5), 2.60–2.80 (m, 2H-7,6), 2.90–3.16 (m, 2H-7,2), 3.19 (dd, ²J=13 Hz, ³J=10 Hz, 1H-6), 3.96 (bd, ³J=6 Hz, 1H-9), 4.05 (bd, ³J=9 Hz, 1H-9), 5.03 (ddd, ²J=1 Hz, ³J$_{cis}$=11 Hz, ⁴J=1 Hz, 1H-11), 5.04 (ddd, ²J=1 Hz, ³J$_{trans}$=17 Hz, ⁴J=1 Hz, 1H-11), 5.77–5.98 (m, 1H-10). ¹³C NMR (50 MHz, BB, CDCl₃): δ=24.84 (C-3), 27.39 (C-4), 27.69 (C-8), 27.79 (3Me), 39.60 (C-5), 41.02 (C-7), 54.42 (C-2), 55.56 (C-6), 66.80, 67.25, 67.70 (C-9), 81.98 (4° C.), 114.50 (C-11), 141.56 (C-10), 153.71 (C=O). MS-MAT (RT): m/z (%): 268 (27) [M⁺], 258 (2), 227 (2), 212 (9), 195 (13), 180 (3), 171 (11), 160 (18), 151 (27), 145 (3), 136 (100), 130 (5), 117 (11), 110 (9), 96 (9), 82 (17), 73 (17). HRMS calculated for C₁₅H₂₄DNO₃: 268.1896, found 268.1896.

Data for 3-D: see above.

Applicants herein incorporate by reference in its entirety German Application 196 04 395.6 filed Feb. 7, 1996, which is the priority document of the instant application.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A process for cleaving cinchona alkaloids to a quinoline derivative and an enantiomerically pure, functionalized 1-azabicyclo(2.2.2)octane, which comprises treating a cinchona alkaloid with a complex metal hydride while simultaneously oxidizing by exposure to air in an anhydrous organic solvent.

2. A process as claimed in claim 1, wherein the complex metal hydride comprises lithium alkoxyaluminum hydride or lithium aluminum hydride.

3. Enantiomerically pure 1-azabicyclo(2.2.2)octanes of the formula

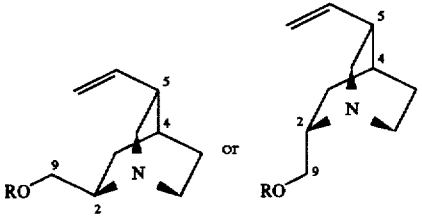

in which R is hydrogen, a straight-chain or branched alkoxycarbonyl group with 1 to 12 carbon atoms, a straight-chain or branched alkyl group with 1 to 12 carbon atoms, alkylated silyl groups, or a substituted phenyl or benzyl substituent.

4. An enantiomerically pure 1-azabicyclo(2.2.2)octane as claimed in claim 3, wherein R is tert-butyldimethylsilyl.

5. An enantiomerically pure 1-azabicyclo(2.2.2)octane as claimed in claim 3, which is (2R,5R)-2-(t-butoxycarbonyloxymethyl)-5-ethenyl-1-azabicyclo(2.2.2)octane (2b).

6. An enantiomerically pure 1-azabicyclo(2.2.2)octane as claimed in claim 3, which is (2R,5R,9R/S)-2-(t-butoxycarbonyloxymethyl)-9-deuterio-5-ethenyl-1-azabicyclo(2.2.2)octane (4a, 4b).

7. An enantiomerically pure 1-azabicyclo(2.2.2)octane as claimed in claim 3, which is (2S,5R)-2-(t-butoxycarbonyloxymethyl)-5-ethenyl-1-azabicyclo(2.2.2) octane (6b).

8. An enantiomerically pure 1-azabicyclo(2.2.2)octane as claimed in claim 3, which is (2S,5R,9R/S)-2-(t- butoxycarbonyloxymethyl)-9-deuterio-5-ethenyl-1-azabicyclo(2.2.2)octane (7a, 7b).

9. A process as claimed in claim 1, wherein the organic solvent comprises an ether.

10. A process as claimed in claim 1, wherein the organic solvent comprises tetrahydrofuran.

* * * * *